United States Patent [19]

Narayan et al.

[11] Patent Number: 5,170,789
[45] Date of Patent: Dec. 15, 1992

[54] INSERTABLE NMR COIL PROBE

[76] Inventors: Perinchery Narayan, 325 San Leandro Way, San Francisco, Calif. 94127; Marcus W. Hedgcock, Jr., 32 Flint St.; Charles M. Anderson, 524 Elizabeth St., both of San Francisco, Calif. 94114

[21] Appl. No.: 416,628

[22] Filed: Oct. 3, 1989

Related U.S. Application Data

[63] Continuation-in-part of Ser. No. 326,509, Mar. 20, 1989, abandoned, which is a continuation of Ser. No. 63,109, Jun. 17, 1987, abandoned.

[51] Int. Cl.$^5$ .............................................. A61B 5/055
[52] U.S. Cl. .................................. 128/653.5; 324/318
[58] Field of Search .......... 128/653 A, 653 SC, 653.2, 128/653.5; 324/318, 322

[56] References Cited

U.S. PATENT DOCUMENTS

| | | | |
|---|---|---|---|
| 3,757,773 | 9/1973 | Kolin | 128/692 |
| 4,446,431 | 5/1984 | McKay | 324/322 |
| 4,592,341 | 6/1986 | Omagari et al. | 604/264 |
| 4,633,181 | 12/1986 | Murphy-Boesch et al. | 324/322 |
| 4,645,491 | 2/1987 | Evans | 604/158 |
| 4,672,972 | 6/1987 | Berke | 128/653 SC |
| 4,692,139 | 9/1987 | Stiles | 604/22 |
| 4,932,411 | 6/1990 | Fritschy et al. | 128/653 A |
| 5,050,607 | 9/1991 | Bradley et al. | 128/653.2 |

Primary Examiner—Ruth S. Smith
Attorney, Agent, or Firm—Flehr, Hohbach, Test, Albritton & Herbert

[57] ABSTRACT

A nuclear magnetic resonance (NMR) imaging method and apparatus is disclosed. The apparatus is an insertable probe consisting of a handle portion and an insertable portion. The probe has a NMR signal receiver disposed within the insertable portion and a reception frequency tuner which may be connected to an actuator which extends outside the sample into which the probe has been inserted. The NMR method of this invention includes the steps of inserting a NMR probe at a preselected detection location in a cavity within a sample, placing the sample in an external magnetic field, applying a perturbation pulse to the sample, and using the probe to receive the NMR emissions from the sample.

6 Claims, 4 Drawing Sheets

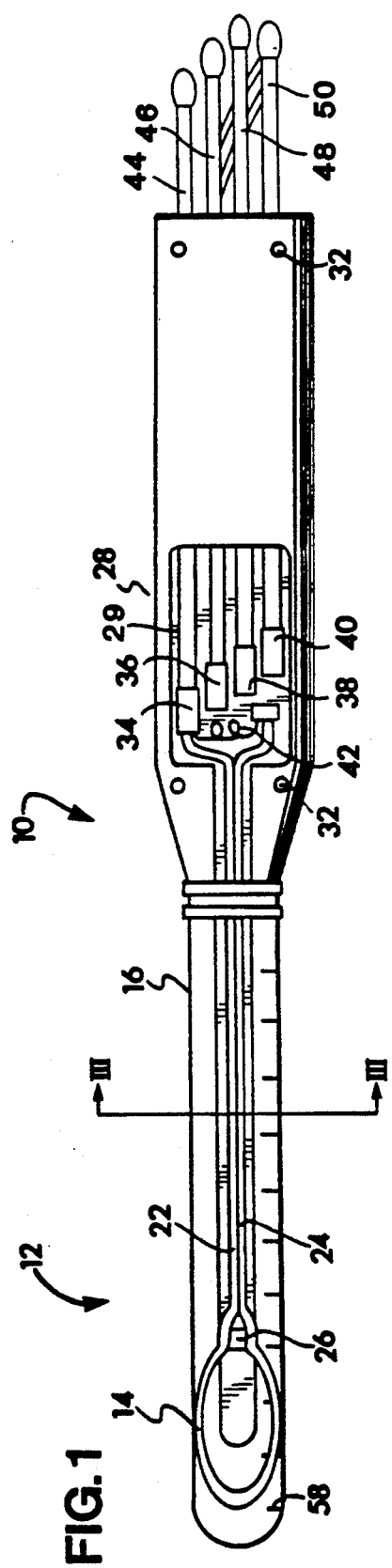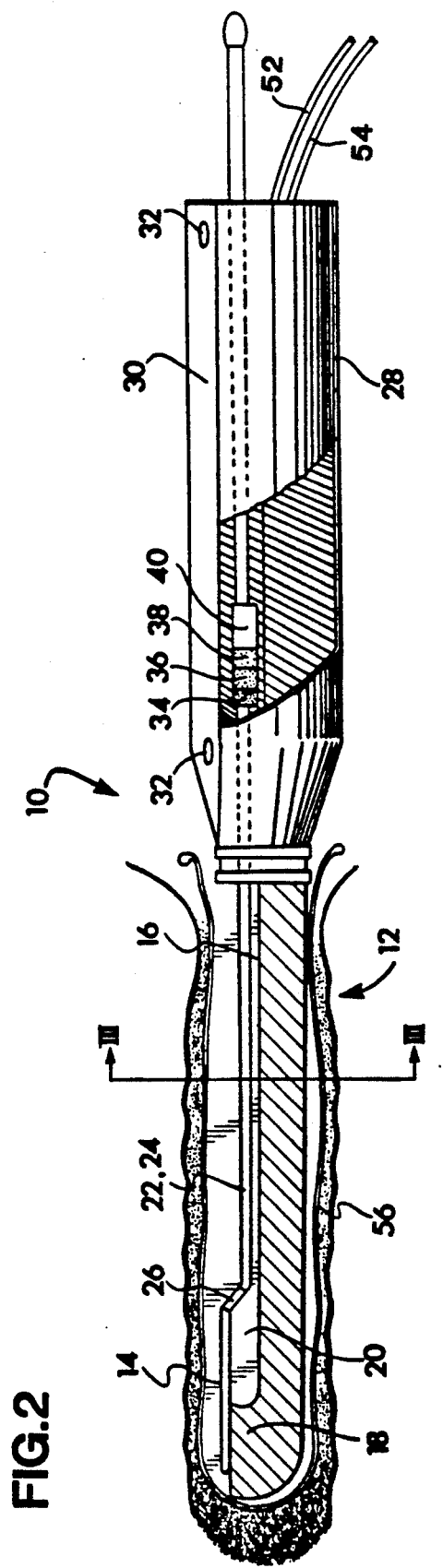
FIG.1
FIG.2

FIG.3
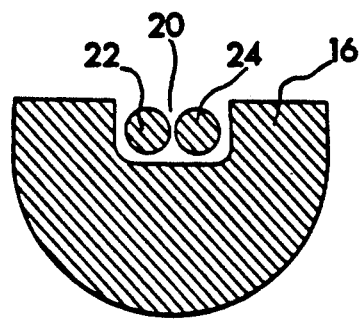
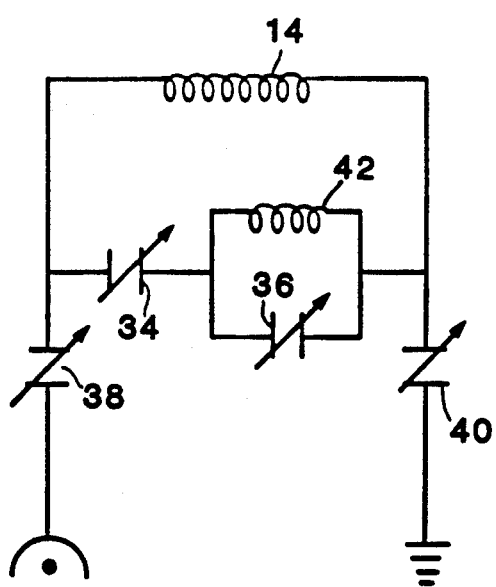
FIG.4
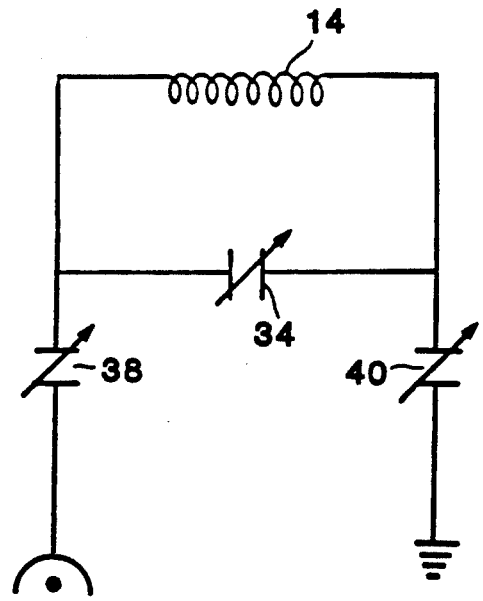
FIG.5

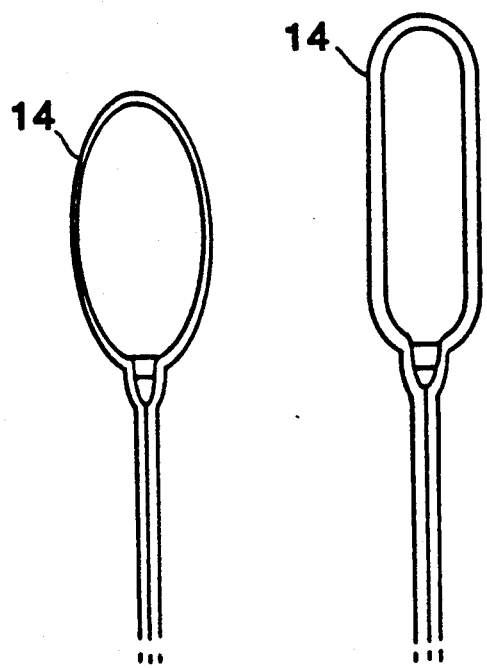
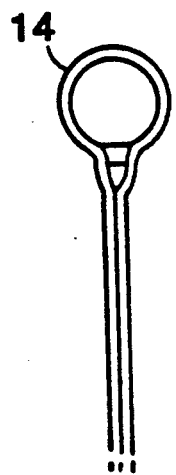
FIG.6 FIG.7 FIG.8
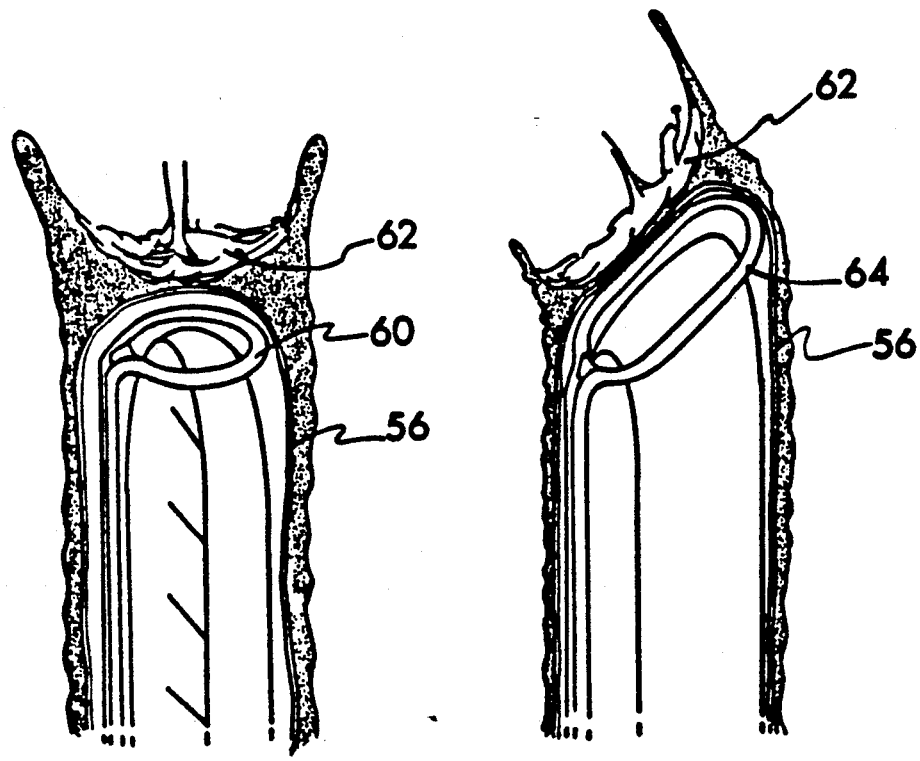
FIG.9 FIG.10

INSERTABLE NMR COIL PROBE

BACKGROUND OF THE INVENTION

This application is a continuation-in-part of U.S. patent application Ser. No. 07/326,509, filed on Mar. 20, 1989, which is a continuation of U.S. patent application Ser. No. 07/063,109, filed on Jun. 17, 1987, both abandoned.

This invention relates to probes operating on the principle of nuclear magnetic resonance imaging (NMRI) and spectroscopy (NMRS). Such probes are useful for studying the structure and biochemistry of normal and abnormal tissues in deeply located organs such as the rectum, colon, prostate, bladder, cervix or any tissue in close proximity to these or other internal organs.

The use of NMRI and NMRS for studying normal and abnormal body tissues is common in the medical field. When an object or substance is placed in a magnetic field, the nuclear magnetic moments in the object or substance align with the field, either in a low energy (parallel to the field) or high energy (anti-parallel) state. If a radio frequency pulse is then applied with energy corresponding to the difference between the two states, the pulse induces transitions between the two states with the result that more nuclei will be found in a high energy state than before. This effect is referred to as the nuclear magnetic resonance phenomenon.

The frequency of the electromagnetic pulse inducing the transitions depends upon the type of nucleus and the chemical environment of the nuclei. Each type of nucleus, such as hydrogen, carbon or phosphorus, in a given chemical environment, has a characteristic electromagnetic wave frequency. The frequency at which transitions are induced can be shown as spectra, which are plots of the resonance intensity as a function of frequency. By looking at the shape of a spectrum different chemical species can be identified by their characteristic frequency. The spatial location of the nuclei may also be determined and plotted as an image that is characteristic for the particular tissue.

One prior art application of nuclear magnetic resonance technology is shown by U.K. patent application no. 2 039 055 (Damadian). This reference discloses an NMR device in which the specimen to be analyzed is placed within a donut-shaped magnet. Surrounding the specimen is a series of field focusing coils. A resonance frequency is supplied by a conventional adjustable radio frequency oscillator surrounding the specimen. The direction of the oscillating magnetic field provided by the oscillator is orthogonal to the direction of the primary static magnetic field. The oscillating signal induces energy level transitions in the specimen. When the oscillating signal ceases, the energized specimen emits the energy it absorbed. The NMR signals emitted by the specimen are detected by the oscillating coil and transmitted to a spectrometer for processing. A computer processes the signals to generate a cross-sectional view of the specimen.

Another prior art NMR device is disclosed by U.S. Pat. No. 4,592,363 to Krause, the disclosure of which is incorporated herein by reference. The Krause apparatus differs from the Damadian apparatus in that the coil generating the oscillating signal is shaped in such a manner that the sensitivity of the coil can be adjusted in the depth direction. However, while this design enables resonance signals from deeper parts of the body to be obtained, it lacks the sensitivity to provide an accurate picture of regions deep within the body.

SUMMARY OF THE INVENTION

One problem with prior art external NMR devices is their depth sensitivity. For example, when using an external NMR device to examine a human patient for tumors located in deep regions of the body, emission signals from the surface of the patient interfere with signals from the interior of the patient. Thus, the utility of prior art external NMR devices to examine regions substantially below the surface of the specimen is limited. What is needed, therefore, is an NMR device which can be used to analyze the interior of a specimen or patient.

This invention meets this need by providing an NMR emissions detection mechanism or probe which may be inserted into the patient or sample. The probe has an adjustable tuning circuit and may be tuned to a desired detection frequency. To use the probe, the subject is placed within a magnetic field, and an external radio frequency pulse is directed at the sample. The probe is placed at an appropriate position within a body cavity to detect emissions from the sample as the sample returns from its high energy state to its low energy state. The probe may also use the emissions detection mechanism as the source of the radio frequency pulse.

BRIEF DESCRIPTION OF THE DRAWINGS

FIG. 1 is an top elevational and partial sectional view of one preferred embodiment of the invention.

FIG. 2 is a side elevational and partial sectional view of the embodiment of FIG. 1.

FIG. 3 is a sectional view of the plane III—III shown in FIGS. 1 and 2.

FIG. 4 is a circuit diagram of the variable capacitor circuit according to one embodiment of the invention.

FIG. 5 is a circuit diagram of the variable capacitor circuit according to another embodiment of the invention.

FIG. 6 is a view showing one type of coil used in the probe.

FIG. 7 is a view showing another type of coil which may be used in the probe of this invention.

FIG. 8 is a view showing yet another type of coil which may be used in the probe of this invention.

FIG. 9 is a view of a probe with a coil perpendicular to the longitudinal axis of the probe.

FIG. 10 is a view of a probe with a coil at an acute angle with respect to the longitudinal axis of the probe.

DETAILED DESCRIPTION OF THE PREFERRED EMBODIMENT

Figures 11, 12, 13:
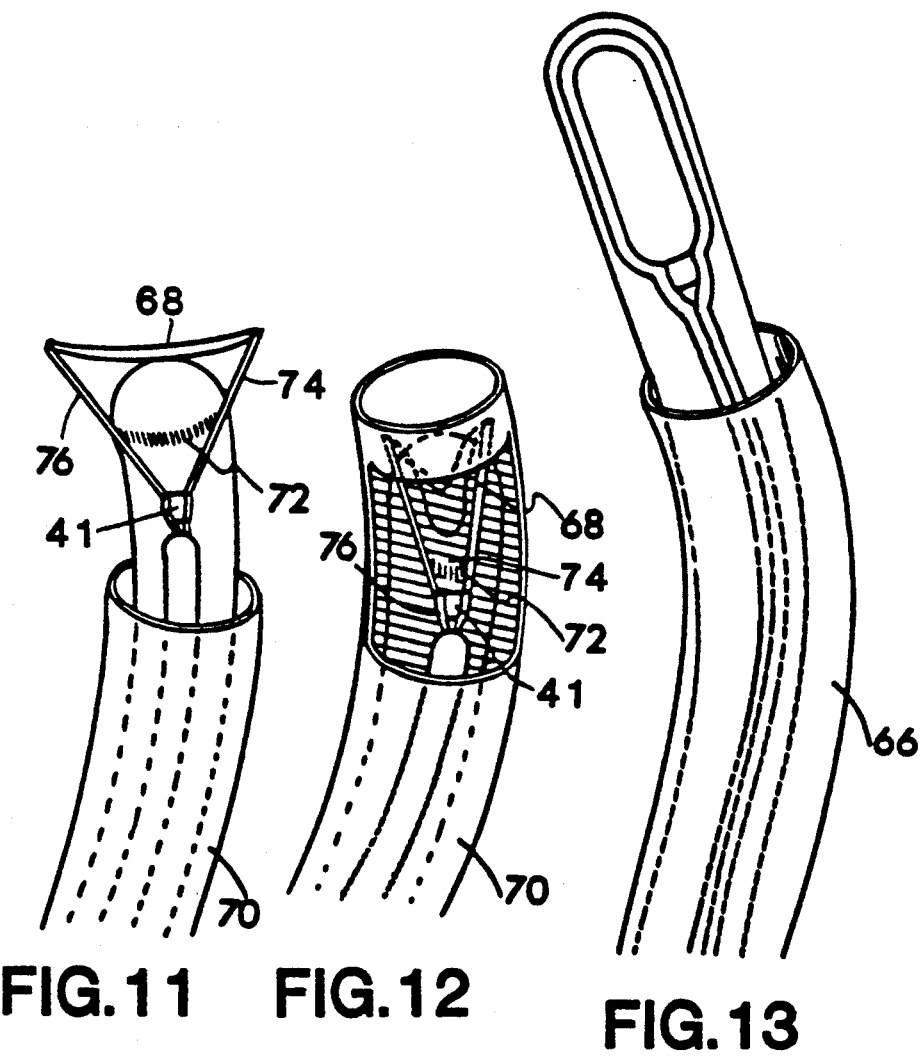
FIG. 11 is a view of an expandable coil for endoscopic use with the coil in its expanded operating position projecting from the endoscope.
FIG. 12 is a view of the expandable coil of FIG. 11 in a collapsed position within the endoscope.
FIG. 13 is a view of an endoscopic probe with a flexible housing.

The probe 10 shown in FIGS. 1 and 2 consists of an insertable portion 12 and a handle portion 28. Both insertable portion or probe section 12 and handle portion 28 are made of plastic or from any other suitable material.

Disposed within insertable portion 12 is a coil 14 made from copper or from any other suitable conducting material. The shape of coil 14 may be oval as shown in FIG. 1, or any other suitable shape.

Insertable portion 12 has a flat surface 16 which is elevated at its front end 18 to provide a support for coil 14. Flat surface 16 also has a central longitudinal groove 20 in which two leads 22 and 24 are disposed. Leads 22 and 24 are in electrical contact with coil 14 and run from coil 14 to the interior portion of handle 28. A ceramic chip capacitor 26 is disposed between leads 22 and 24 at the point of their connection to coil 14. Capacitor 26 serves to prevent signal distortion caused by the proximity of the two leads in the measurement area and to isolate the coil signal from noise generated by the leads. Copper tape (not shown) is affixed to probe 10 just below and to the sides of coil 14 as a radio frequency shield.

Handle 28 has a cylindrical shape. In the preferred embodiment, a removable cover 30 is attached by four screws 32. Disposed within a rectangular cavity (not shown) in handle 28 are four identical variable capacitors 34, 36, 38 and 40 which form part of the balanced-matched, double-tuned probe circuit.

The use of adjustable capacitors to tune and match a resonator circuit is known in the art. For example, U.S. Pat. No. 4,634,980 to Misic, et al. discloses one such circuit. Another circuit is disclosed in U.S. Pat. No. 4,446,431 to McKay. The disclosures of these references are incorporated herein by reference.

The tuning and matching circuits according to the preferred embodiment of this invention are shown in FIGS. 4 and 5. As shown in FIG. 4, a capacitor unit for a double tuned coil consists of four variable capacitors 34, 36, 38 and 40. Preferably, the capacitors are 1-30 pF capacitors manufactured by The Johanson Company of Boonton, New Jersey, although any equivalent capacitor may be used.

Element 14 in FIG. 4 corresponds to sample coil 14 of FIGS. 1 and 2, and element 42 corresponds to induction coil 42 of FIG. 1. In the preferred embodiment, sample coil 14 is a 2 cm rigid coil made of 3 mm copper wire. The characteristics of induction coil 42 may be chosen to meet the desired operating parameters of the probe as discussed below.

Coil 14 can be tuned to the desired resonant frequency by capacitor 34. Capacitor 38 is used to match the impedance of the probe circuit with the impedance of the sample. Capacitor 40 balances coil 14 with respect to ground, thereby minimizing dielectric losses caused by the conductivity of the sample.

Coil 42 and capacitor 36 form a trap circuit which enables coil 14 to be tuned at two different frequencies. The inductance of coil 42 is selected to optimize the frequencies at which coil 14 is tuned. For example, the 2 cm coil of 3 mm copper wire discussed above as element 14 may be tuned to the frequencies for hydrogen and phosphorus.

FIG. 5 shows a circuit diagram of a variable capacitor unit for a single-tuned coil 14. This circuit differs from the circuit shown in FIG. 4 in that there is no inductor coil 42 and only three capacitors: 34, 38 and 40. As with the circuit shown in FIG. 4, capacitor 34 is used to tune coil 14, capacitor 38 is used to match the impedance of the circuit with the sample impedance, and capacitor 40 balances coil 14 with respect to ground, thereby minimizing dielectric losses caused by the conductivity of the sample.

As shown in FIG. 1, a movable part of capacitors 34, 36, 38 and 40 is connected to four studs or actuators 44, 46, 48 and 50, respectively. Studs 46-50 are threaded and extend through threaded holes (not shown) in the rear of handle portion 28. Studs 44-50 may have any length convenient for tuning.

Conducting wires 52 and 54 extend through the rear of handle portion 28 and are connected to an oscilloscope or NMR instrument (not shown). Probe 10 is provided with a scale 58 which shows the approximate position and orientation of coil 14 within the patient and thus the position of the inspected area.

The size and shape of insertable portion 12 is not critical and can vary within a wide range. For example, for a transrectal straight-type probe as shown in FIGS. 1 and 2, insertable portion 12 may have a length of 25 cm and a semicircular cross-sectional diameter of about 3 cm.

FIG. 9 shows an insertable portion 12 of a probe designed especially for examining the cervix. In this embodiment, insertable portion 12 contains a coil 60 adjacent the tip of insertable portion 12 and oriented in a plane which is perpendicular to the axis of the probe. The rest of the probe is identical to and operates in the same manner as the rectal probe.

Alternatively, the probe may be disposed within a flexible housing as shown in FIGS. 11-13, such as in a sigmoidoscope 66 or an endoscope 70. The sigmoidoscope of FIG. 13 is intended for analyzing colonic tissues and tumors. In the embodiment of FIGS. 11 and 12, on the other hand, an expandable coil 68 is inserted into the endoscopic instrument 70. A compression spring 72 is located between leads 74 and 76 which connect coil 68 to capacitor unit 41. Spring 72 constantly urges leads 74 and 76 apart so as to keep coil 68 in an expanded or operating position. The probe is inserted into endoscope 70 which confines the coil and keeps it in the closed position until the instrument reaches the proper position. The probe is then moved forward with respect to endoscope 70 so that leads 74 and 76 and coil 68 project beyond the tip of endoscope 70, and spring 72 expands coil 68 to the position shown in FIG. 11, i.e., into an operative position substantially perpendicular to the axis of the probe within the organ being examined.

The shape and orientation of coil 14 may vary with the application. FIGS. 6-8 show alternative shapes for coil 14. Each of the coils shown in the those FIGURES can be used within a probe of the type shown in FIGS. 1-3.

To use the instrument of this invention to receive NMR emissions from a subject location within a patient, a condom 56 is placed around the insertable portion 12. The function of the condom is to prevent cross-contamination between patients during multiple uses of the probe. The condom also serves to protect the coil from moisture and will not interfere with magnetic signals between the inspected tissue and coil 14. Insertable portion 12 is then inserted in a body cavity such as the rectum at a detection location which places coil 14 adjacent the subject location.

Prior to operation of the probe, it is tuned, matched and balanced. Conducting wires 52 and 54 are connected in parallel to the input terminal of a pulse generator and an oscilloscope, respectively (not shown). The probe is then tuned, matched and balanced to a desired frequency by selectively rotating threaded studs 44, 48 and 50, respectively, of variable capacitors 34, 38 and 40. The results of the tuning and matching operation can be seen on the oscilloscope or NMR instrument.

The whole body of a patient is placed in a magnetic field and coil 14 is activated. A radio-frequency perturbation pulse of a predetermined frequency and duration is then applied to the magnetic field. The frequency of the pulse is selected to match the desired resonant frequency to which the coil 14 has been tuned. As is known in the art, different resonant frequencies, such as the frequencies for carbon, hydrogen, phosphorus or sodium, are used for different kinds of tissues or different tests. The energy from the radio frequency perturbation pulse will be absorbed by the tissues surrounding coil 14. Immediately after the end of the perturbation pulse, the tissue surrounding coil 14 will emit electromagnetic energy. These electromagnetic wave signals are detected by coil 14 and are transmitted to an external NMR instrument where they can be measured in a conventional manner to produce spectra in images.

In addition to its function as a detection coil, coil 14 may also be used as an antenna to transmit the radio-frequency pulse. When used in that manner, coil 14 is connected to both the external pulse generating circuit and the external detection and analysis circuit of the NMR instrument. The detection circuit begins detecting the electromagnetic signals from the sample after the perturbation pulse ends.

Other modifications within the scope of this invention will be apparent to those of ordinary skill in the art.

What is claimed is:

1. A nuclear magnetic resonance probe assembly for use in examining tissue in an organ within the human body, comprising an axially extending handle, an elongated probe section extending axially from the handle for insertion into the body to the organ to be examined and having a proximal end portion located adjacent to the handle and a distal end portion located remotely from the handle, a pair of axially extending leads carried by the distal end portion of the probe section, a coil comprising a flexible loop connected to the leads for movement between a collapsed position for insertion into the body and an extended position for receiving a nuclear magnetic resonance signal from the tissue in the organ, a compression spring connected between the leads urging the leads apart and thereby urging the coil toward the extended position, and means operable externally of the body for holding the coil in the collapsed position.

2. The probe assembly of claim 1 wherein the means for holding the coil in the collapsed position comprises a tubular member which surrounds the leads and holds the leads together while the probe is being inserted into the body and is movable to a retracted position in which the leads project from the tube and can move apart to expand the coil.

3. A nuclear magnetic resonance probe assembly for use in examining tissue in an organ within the human body, comprising an axially extending handle, an elongated probe section extending axially from the handle for insertion into the body to the organ to be examined and having a proximal end portion located adjacent to the handle and a distal end portion located remotely from the handle, means carried by the distal end portion of the probe section for receiving a nuclear magnetic resonance signal from the tissue in the organ, a plurality of tuning elements within the handle connected electrically to the receiving means and forming a circuit for tuning the probe for response to a signal of desired frequency, and actuators connected to the tuning elements and extending in an axial direction from an end of the handle opposite the probe section for adjusting the response frequency.

4. The probe assembly of claim 3 wherein the receiving means comprises a coil, and the tuning elements comprise variable capacitors.

5. The probe assembly of claim 4 wherein the actuators comprise studs which are threadedly received in the end of the handle.

6. The probe assembly of claim 3 including a scale on the probe section for visually indicating the positioning of the probe section in the body.

* * * * *